US012270788B2

(12) United States Patent
Ooi et al.

(10) Patent No.: US 12,270,788 B2
(45) Date of Patent: Apr. 8, 2025

(54) VERSATILE OPTICAL FIBER SENSOR AND METHOD FOR DETECTING RED PALM WEEVIL, FARM FIRES, AND SOIL MOISTURE (71) Applicant: KING ABDULLAH UNIVERSITY OF SCIENCE AND TECHNOLOGY, Thuwal (SA)

(72) Inventors: Boon Siew Ooi, Thuwal (SA); Yuan Mao, Thuwal (SA); Islam Ashry, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 388 days.

(21) Appl. No.: 17/637,684

(22) PCT Filed: Aug. 21, 2020

(86) PCT No.: PCT/IB2020/057865
§ 371 (c)(1),
(2) Date: Feb. 23, 2022

(87) PCT Pub. No.: WO2021/038407
PCT Pub. Date: Mar. 4, 2021

(65) Prior Publication Data
US 2022/0283022 A1 Sep. 8, 2022

Related U.S. Application Data (60) Provisional application No. 62/892,653, filed on Aug. 28, 2019.

(51) Int. Cl.
*G01N 29/14* (2006.01)
*G01D 5/353* (2006.01)
(Continued)

(52) U.S. Cl.
CPC ......... *G01N 29/14* (2013.01); *G01D 5/35316* (2013.01); *G01D 5/35361* (2013.01);
(Continued)

(58) Field of Classification Search
CPC .......... G01D 5/35383–35396; G01D 5/35316; G01D 5/35361; G01D 5/35364;
(Continued)

(56) References Cited

U.S. PATENT DOCUMENTS 6,795,599 B2 * 9/2004 Spirin ..................... G01L 1/246
385/12
7,199,869 B2 * 4/2007 MacDougall ...... G01D 5/35354
356/73.1
(Continued)

FOREIGN PATENT DOCUMENTS

CN 108663138 A * 10/2018
EP 3467495 A1 * 4/2019
(Continued)

OTHER PUBLICATIONS

Soroker et al., "Early Detection and Monitoring of Red Palm Weevil: Approaches and Challenges," AFPP—Palm Pest Mediterranean Conference, Nice, Jan. 16-18, 2013 (Year: 2013).*
(Continued)

*Primary Examiner* — Judy Nguyen
*Assistant Examiner* — James Split
(74) *Attorney, Agent, or Firm* — PATENT PORTFOLIO BUILDERS PLLC (57) ABSTRACT An integrated system for detecting a red palm weevil (RPW), farm fire, and soil moisture includes an optical fiber configured to be extending to a tree, and a distributed acoustic sensor (DAS) box connected to the optical fiber. The DAS box is configured to process first to third different optical signals reflected from the optical fiber, to determine
(Continued)

a presence of the RPW from the first optical signal, a temperature at a location along the optical fiber from the second optical signals, and a moisture at a location around the tree from the third optical signal.

17 Claims, 10 Drawing Sheets

(51) Int. Cl.
*G01H 9/00* (2006.01)
*G01N 29/24* (2006.01)
*G01N 33/00* (2006.01)
*A01G 7/00* (2006.01)

(52) U.S. Cl.
CPC ......... *G01D 5/35364* (2013.01); *G01H 9/004* (2013.01); *G01N 29/2418* (2013.01); *G01N 33/0098* (2013.01); *A01G 7/00* (2013.01); *G01N 2291/0238* (2013.01)

(58) Field of Classification Search
CPC ......... G01D 5/35358; G01H 9/00–008; G01N 29/14; G01N 29/2418; G01N 2291/0238; G01N 33/0098; A01M 1/026; A01G 7/00–06

See application file for complete search history.

(56) References Cited

U.S. PATENT DOCUMENTS

| | | | |
|---|---|---|---|
| 10,634,553 B1 * | 4/2020 | Hveding | ............... G01H 9/004 |
| 10,880,007 B1 * | 12/2020 | Hveding | ............ G02B 6/29361 |
| 2013/0008253 A1 | 1/2013 | Tsuda | |
| 2015/0114127 A1 | 4/2015 | Barfoot et al. | |
| 2019/0025095 A1 | 1/2019 | Steel et al. | |

FOREIGN PATENT DOCUMENTS

| | | | |
|---|---|---|---|
| IT | 102020000030056 B1 * | 12/2022 | |
| JP | H0420824 A | 1/1992 | |
| WO | 2004074821 A1 | 9/2004 | |
| WO | 2020217160 A1 | 10/2020 | |

OTHER PUBLICATIONS

Substantive Examination Report in corresponding/related Saudi Arabian Application No. 522431759, dated Jun. 25, 2023.

Ma, X., et al., "Using Multiple Reference Points in Raman Based Distributed Temperature Sensor for Eliminating DC Interference," IEEE Sensors Journal, Jan. 2014, vol. 14, pp. 295-301, IEEE.

Aleksic, S., "Optical Technologies: An Important Enabler for Smart Systems and Infrastructures," 2019 15th International Conference on Telecommunications (CONTEL), Jul. 3, 2019, pp. 1-8, IEEE.

Ashry, I., et al., "Normalized Differential Method for Improving the Signal-to-Noise Ratio of a Distributed Acoustic Sensor," Applied Optics, Jun. 20, 2019, vol. 59, No. 18, pp. 4933-4938, Optical Society of America.

Bolognini, G., et al., "Raman-Based Fibre Sensors: Trends and Applications," Optical Fiber Technology, Dec. 2013, vol. 19, No. 6, pp. 678-688.

Bremer, K., et al., "Fibre Optic Humidity Sensor Designed for Highly Alkaline Environments," Proceedings of SPIE, IEEE, US, May 22, 2014, vol. 9157, pp. 9157A4-9157A4 (4 pages).

Chen, Y., et al., "A Nonlinear Mirror Structure to Increase the Performance of the Distributed Fiber Temperature Sensor Based on Raman Backscattering," Optical Fiber Sensors Conference, 2008, APOS '08, 1st Asia-Pacific, IEEE, Piscataway, NJ, USA, Nov. 7, 2008, pp. 104.

Ezzedine, T., et al., "Efficient Measurement of Temperature, Humidity and Strain Variation by Modeling Reflection Bragg Grating Spectrum in WSN," Optik, Jan. 24, 2017, vol. 135, pp. 454-462, Elsevier GmbH.

International Search Report in corresponding/related International Application No. PCT/IB2020/057865, date of mailing Nov. 4, 2020.

Mao, Y., et al., "Towards Early Detection of Red Palm Weevil Using Optical Fiber Distributed Acoustic Sensor," 2019 Optical Fiber Communications Conference and Exhibition (OFC), OSA, Mar. 3, 2019, pp. 1-3.

Pradhan, H.S., et al., "A Survey on the Performances of Distributed Fiber-Optic Sensors," International Conference on Microwave, Optical and Communication Engineering, Dec. 18-20, 2015, pp. 243-246, IEEE.

Written Opinion of the International Searching Authority in corresponding/related International Application No. PCT/IB2020/057865, date of mailing Nov. 4, 2020.

* cited by examiner

VERSATILE OPTICAL FIBER SENSOR AND METHOD FOR DETECTING RED PALM WEEVIL, FARM FIRES, AND SOIL MOISTURE

CROSS-REFERENCE TO RELATED APPLICATIONS

This application is a U.S. National Stage Application of International Application No. PCT/IB2020/057865, filed on Aug. 21, 2020, which claims priority to U.S. Provisional Patent Application No. 62/892,653, filed on Aug. 28, 2019, entitled "VERSATILE OPTICAL FIBER SENSOR FOR DETECTING RED PALM WEEVIL, FARM FIRES, AND SOIL MOISTURE," the disclosures of which are incorporated herein by reference in their entirety.

BACKGROUND

Technical Field

Embodiments of the subject matter disclosed herein generally relate to a system and method that use an optical fiber for detecting red palm weevils, and more particularly, to an enhanced system that processes data recorded with the optical fiber, which is wrapped around a red palm, to detect not only the presence of the red palm weevils, but also an ambient temperature and moisture.

Discussion of the Background

Red palm weevil (RPW) (*Rhynchophorus ferrugineus*) is a snout pest originating from tropical Asia. In the past few decades, it has spread out to many regions worldwide including North Africa, Middle East, and Mediterranean regions. This pest has wiped out many palm farms in different countries, so it is considered a very severe problem. In the Gulf countries and the Middle East, millions of dollars are spent yearly only to remove the infested palm trees. The cost to treat the infested palm trees could be even higher. Additionally, by 2023, it is estimated that RPW control cost and loss of benefits to be in the millions of dollars in Italy, Spain, and France.

The problem with this pest is that although there are available techniques to heal RPW infested palm trees, detecting the presence of the RPW threat at an early stage (first two/three weeks of the weevil larvae stage) is challenging. This is so because by the time a palm tree shows visible signs of distress, such as a sagging canopy, this generally means that the RPW infection is well-advanced and it is too late to rescue the tree. As a result, governments of many countries are committing to develop a reliable and efficient early detection approach to tackle this problem.

There are several methods that have been reported to tackle this sever danger. For instance, trained dogs are used to smell the gases released from infested palms during the fermentation processes. Unfortunately, sensing such kind of gases is not an accurate selective process because its efficiency is impacted by the presence of other volatile products. Alternatively, infested trees are screened with a computer-based tomography system. However, this technique lacks feasibility since it is slow and expensive.

The first detectable signals of an infested tree originate from the noise produced by the weevil larvae while eating within the trunk of the tree. Therefore, the most promising early detection methods rely on using acoustic sensors. The existing technologies mainly insert a sound probe into the tree trunk such that the probe records larvae sound in real-time.

Figure 1:
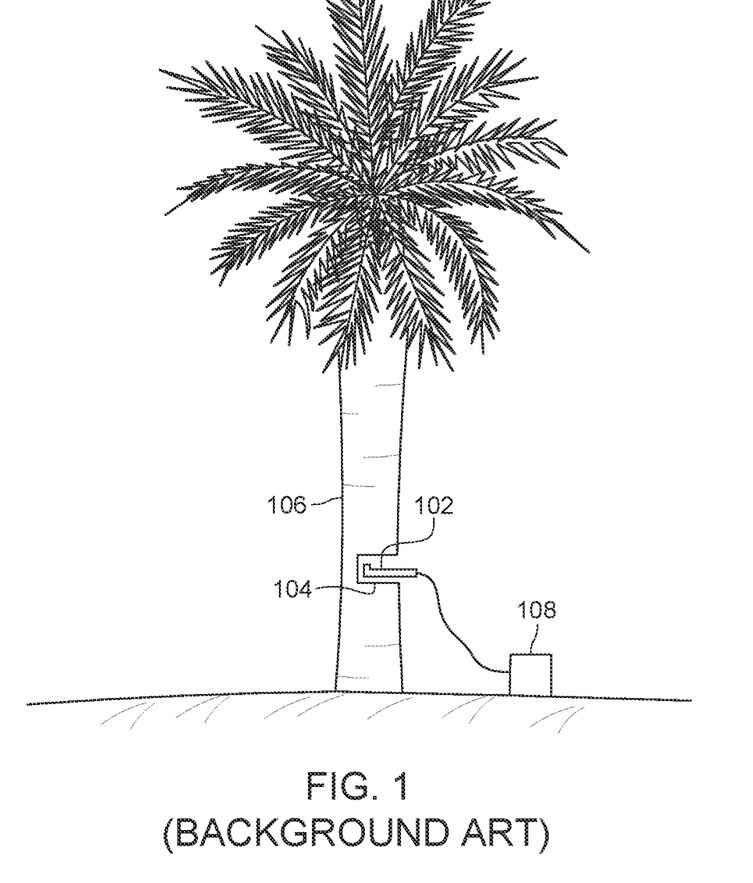
FIG. 1 is a schematic diagram of a red palm tree having its trunk drilled to place an acoustic sensor.

More specifically, the existing methods that use acoustic sensors, as illustrated in FIG. 1, primarily insert an acoustic probe 102, such as microphone, into a hole 104 drilled into a palm trunk 106 and then the probe records the sound produced by the beetles in real-time. The sound is recorded on a computer 108 that is connected to the acoustic probe 102. The differences among the methods that are using the acoustic sensor are mainly in the signal processing techniques implemented for processing the recorded sound. However, all these methods require in-situ monitoring.

For vast farms, checking palms one-by-one is labor-, time-, and cost-consuming. Moreover, a major drawback of these reported methods is that they do not offer continuous monitoring for palm trees. An alternative solution is where each palm is equipped with a corresponding sound probe, which is connected to a wireless communication interface so that data transfer can take place to a central server. This system may be powered via a solar panel. Although this method provides continuous observation for the individual palm trees, its overall cost is still very high. Another disadvantage of the aforementioned acoustic methods is the damage done to the tree because of the hole made in the trunk for inserting the sound probe, the labor necessary to drill each tree, the impact of the hole on the growth of the palms, and the possibility of other insects to establish a nest into the holes made into the trunk.

Additionally, offering an acoustic sensor along with a wireless communication interface for each tree to provide continuous monitoring significantly increases the cost of the entire RPW surveillance system given that a red palm tree orchard can have thousands of such trees.

The presence of the RPW is just one concern associated with the palm trees in an orchard. The farmers of these trees are also faced with the potential of fires in the trees, which can destroy many of the trees, especially that these trees thrive in semi-desertic zones, which are prone to fires. In addition, these trees also require the right amount of water for maximizing their crop and saving on the cost associated with watering. Thus, the farmers need in addition to the RPW monitoring system, a fire detection system, and also a moisture detection system to improve the efficiency of the palm tree farm. All these systems are not only expensive, but also require substantial infrastructure support, which is not affordable for the typical farm.

Thus, there is a need for a new integrated system that is capable of detecting not only the presence of the RPW larvae, but also to be able to determine the presence of a fire and the moisture of the ambient of the trees, with minimal infrastructure investment and support. In addition, the new system is expected to not be invasive for the health of the tree.

BRIEF SUMMARY OF THE INVENTION

According to an embodiment, there is an integrated system for detecting a red palm weevil (RPW), farm fire, and soil moisture, and the system includes an optical fiber configured to be extending to a tree, and a distributed acoustic sensor (DAS) box connected to the optical fiber. The DAS box is configured to process first to third different optical signals reflected from the optical fiber, to determine a presence of the RPW from the first optical signal, a temperature at a location along the optical fiber from the second optical signals, and a moisture at a location around the tree from the third optical signal.

According to another embodiment, there is an integrated system for detecting a red palm weevil (RPW), farm fire, and soil moisture, and the system includes an optical fiber configured to be extending to a tree, and a distributed acoustic sensor (DAS) box connected to the optical fiber. The DAS box is configured to process a Rayleigh signal, which is reflected in the optical fiber, to determine a presence of the RPW, process Stokes Raman and Anti-Stokes Raman signals reflected in the optical fiber, to determine a temperature at a location along the optical fiber, and process Fiber Bragg Gratings (FBGs) signals generated by FBGs formed in the optical fiber, to determine a moisture at a location around the tree.

In yet another embodiment, there is a method for detecting a red palm weevil (RPW), farm fire, and soil moisture, and the method includes distributing an optical fiber around a tree, connecting the optical fiber to a distributed acoustic sensor (DAS) box, generating with the DAS box a first optical pulse, transmitting the first optical pulse along the optical fiber, receiving first and second different optical signals, which are reflected from the optical fiber, determining a presence of the RPW from the first optical signal, and determining a temperature at a location along the optical fiber from the second optical signals.

BRIEF DESCRIPTION OF THE DRAWINGS

For a more complete understanding of the present invention, reference is now made to the following descriptions taken in conjunction with the accompanying drawings, in which.

DETAILED DESCRIPTION OF THE INVENTION

The following description of the embodiments refers to the accompanying drawings. The same reference numbers in different drawings identify the same or similar elements. The following detailed description does not limit the invention. Instead, the scope of the invention is defined by the appended claims. The following embodiments are discussed, for simplicity, with regard to a distributed acoustic sensor (DAS) system that is used to determine the presence of a RPW larvae, the temperature around the tree, and also the moisture around the tree. However, the embodiments to be discussed next are not limited to determining the presence of the RPW larvae, the temperature and the moisture around a red palm, but may be applied to any tree infestation caused by a bug, or to other applications in which the temperature and moisture of a subject need to be monitored.

Reference throughout the specification to "one embodiment" or "an embodiment" means that a particular feature, structure or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

According to an embodiment, an optical fiber distributed acoustic sensor (DAS) is introduced as a robust solution for the early detection of RPW, temperature detection, and moisture monitoring. In one implementation, all of the optical/electronic components of such a system, such as a laser, photodetector, amplifier, circulator, etc., are gathered within a single unit, the DAS box, and one or more optical fibers are connected to the DAS box. The one or more optical fibers is wound around one or more of the palm trees, thus forming an optical network. As discussed next, this system is used to distinguish two palm trees, one which is healthy and another one that is infested with an about 12 days old larvae. In addition, the same system is used to monitor the temperature along the optical fiber, and, if desired, to also monitor the moisture along the optical fiber. In comparison to the existing acoustic sensors systems discussed in the Background section, the DAS system is unique by providing noninvasive monitoring, continuous surveillance with relatively low cost, spacious farm area coverage with using a single optical fiber cable, and the additional capability of monitoring the temperature and moisture in the farm. Of course, it is possible to use plural optical fibers with this system.

Prior to discussing the above noted capabilities of the new system, the DAS box is introduced. The underlying operation concept of an optical fiber DAS relies on using a coherent (narrow linewidth) laser source to launch optical pulses into the optical fiber. While a pulse of light is propagating along the optical fiber, this pulse of light can experience a scattering while inside the optical fiber, and then a back pulse is generated and this back pulse propagates in an opposite direction along the optical fiber relative to the original pulse of light. The back pulse can be a Rayleigh scattering when the interaction between the initial pulse of light and the optical fiber is elastic, and/or the back pulse is Stokes Raman and/or Anti-Stokes Raman when the interaction is inelastic. The backscattered pulses (Rayleigh, Stokes-Raman, or Anti-Stokes Raman) propagate backwards along the optical fiber and they are received at the fiber input port of the DAS box for storage and processing. By monitoring the intensity's temporal evolution of the recorded backscattered pulses, it is possible to accurately calculate (1) a position along the optical fiber, which was subjected to an acoustic signal and to determine its frequency, and/or (2) to determine a temperature at a given position along the fiber, and/or (3) to determine a relative moisture along the fiber. Based on these responses, a processing part of the DAS system can be configured to determine whether the RPW is present in the tree, the temperature around the tree, and the moisture next to the tree.

Figure 2:
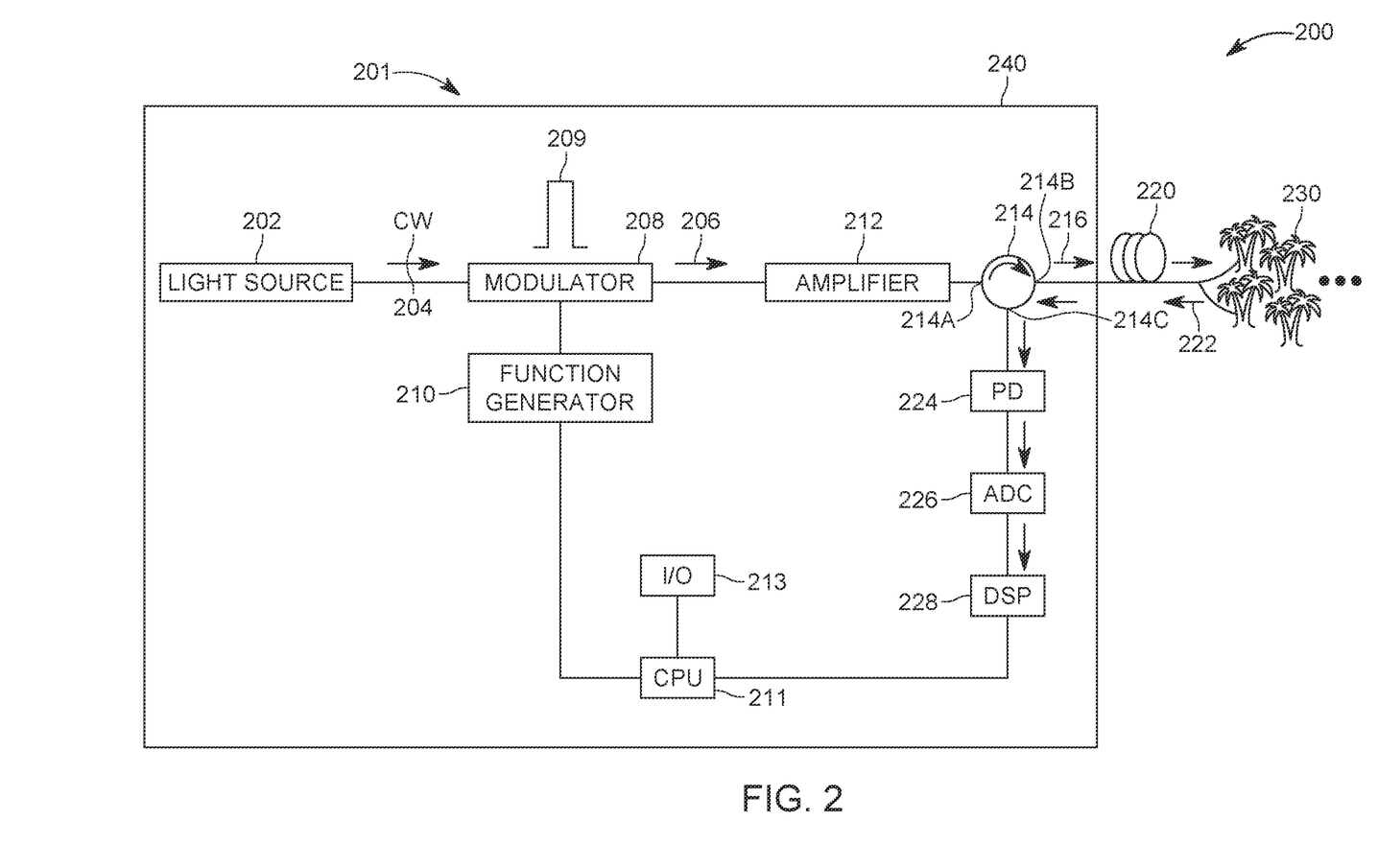
FIG. 2 illustrates a distributed acoustic sensor system that is used to monitor a tree.

In this regard, FIG. 2 shows a fiber optic DAS system 200 that is capable of measuring a strain exerted on the optical fiber by changes in pressure, temperature and/or acoustic noise. System 200 has two main components, the DAS box 201 and the optical fiber 220, which is connected to the DAS box 201. The DAS box 201 includes all the electronics for generating a light beam, sending the light beam into the optical fiber, receiving a reflected light from the optical fiber, and processing the reflected light for detecting the RPW, temperature, and moisture. More specifically, the DAS box 201 includes a light source 202 that is configured to generate continuous-wave (CW) light 204 that is coherent. For example, the light source 202 may be a laser or a light-emitting diode. The CW light 204 is converted to optical pulses 206 via a light modulator 208. The light modulator 208 is connected to a function generator 210. The function generator 210, which can be controlled by a computing device 211, is configured to generate a mathematical function to be applied to the modulator to modulate the light 204. For example, FIG. 2 shows the modulator 208 applying a rectangular pulse 209 to the light 204, to obtain the optical pulses 206 (or modulated light). Other shapes may be used for the pulse 209. The computing device 211 is also connected to an input/output module 213, which is capable of communicating, for example, in a wireless or wired manner with a smartphone, personal computer, or any other electronic device for both sending messages and also for receiving instructions/commands.

Optionally, the system 200 includes an amplifier 212 for amplifying the modulated light 206, prior to launching it through a circulator 214 into the optical fiber 220. FIG. 2 schematically shows the optical fiber 220 being directed to plural trees 230. The circulator 214 may be, for example, a three- or four-port optical device designed such that light entering any port exits from the next port. This means that if light enters a first port 214A, it is emitted from a second port 214B. However, if some of the emitted light 216 is reflected back to the circulator 214, it does not come out of the first port 214A, but instead exits from a third port 214C. This makes possible that a reflected Rayleigh signal 222, after reaching the circulator 214, is directed toward a photodetector 224, instead of being sent toward the amplifier 212.

While the optical pulse 216 is propagating along the fiber 220, the Rayleigh signal 222 is backscattered from the trees 230. In the backward direction, the Rayleigh signal is recorded via the photodetector 224 and then sampled using an analog-to-digital converter (ADC) 226. A digital signal processing (DSP) 228 may be used to filter out the RPW sounds in the frequency domain and exactly identifies the locations of the infected palm trees 230 using, for example, the time domain signal.

The optical fiber 220 may be a single-mode fiber (SMF). At the fiber input port, consecutive Rayleigh backscattered traces are recorded in the time domain. Each Rayleigh trace has a speckle-like profile because of coherent interference of the signals reflected by scattering centers within the injected pulse duration. In the absence of intrusions along the optical fiber, i.e., no refractive index perturbation, the recorded Rayleigh traces are ideally identical. In the case that an acoustic signal is applied at a position along the fiber, such as the weevil larvae sound, the effective refractive index changes at this position and consequently, the intrusion could be sensed by observing the intensity fluctuations of its corresponding speckle in the recorded traces.

By monitoring the intensity temporal evolution of the recorded Rayleigh signals 222, one can accurately figure out a position along the optical fiber 220 which was subjected to an acoustic signal emitted by the RPW and thus, determine the location of the RPW. For the purpose of RPW early detection, the system 200 shown in FIG. 2 outweighs the existing acoustic sensors in the literature because of at least one of the following reasons: 1) it would provide non-stop monitoring for palm trees with a relatively low price, 2) the sensing length of the typical optical fiber DAS is around 10 km, which could cover spacious farm area, 3) by using an optical switch and time-division-multiplexing (TDM), several fibers can be attached to the same DAS box, in case that monitoring larger farm areas is demanded, 4) no invasive sensing is required since the optical fiber would be wounded externally around the palms, and 5) the optical fiber used for acoustic sensing can simultaneously monitor ambient temperatures, with a resolution less than 0.1° C., which is considerably important to control farm fires, which is another major problem around the world.

In one embodiment, all the elements of the system 200, except the optical fiber 220, may be placed in a single housing 240. This means that all of the optical components such as laser, photodetector, etc., are gathered within the DAS box, for example, at a control master station, whereas only the optical fiber 220 is wounded around the palm trees 230 in a form of an optical network.

Figure 3A:
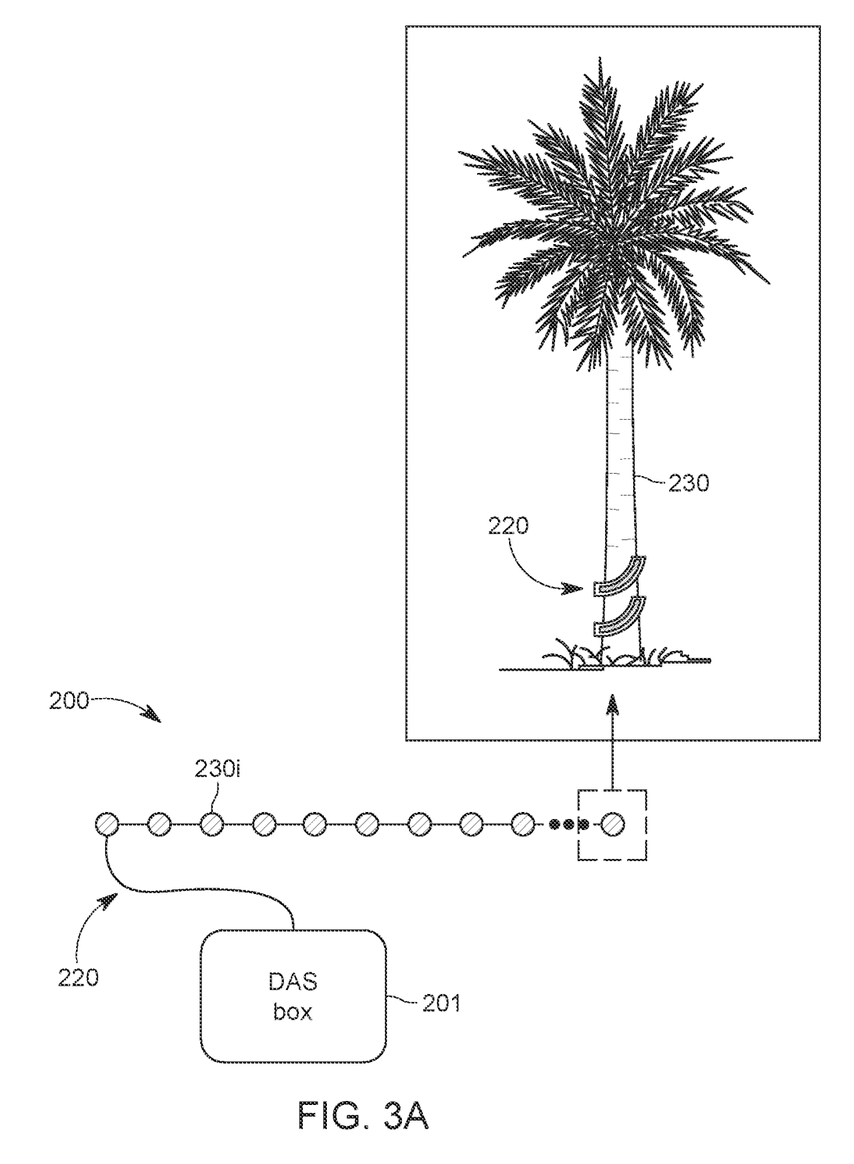
FIGS. 3A to 3E illustrate various implementations of the distributed acoustic sensor system.

The optical fiber 220 can be distributed along one or more trees. For example, FIG. 3A shows an embodiment in which the DAS box 201 is connected to a single optical fiber 220, which extends at plural trees 230$i$, where i is any natural number. The same optical fiber 220 can be rolled around each tree 230$i$, for example, from the ground up to about 1 m height on the trunk of the tree, where the probability of finding the RPW larva is the highest. However, other heights may be used. Between the trees, the optical fiber cable can be either laid down on the ground or buried into the soil, based on the environmental conditions. In another embodiment illustrated in FIG. 3B, a single DAS box 201 and a single optical fiber 220 are used to monitor plural trees 230$i$. However, in this embodiment, the trees are not just a line of trees as in the embodiment of FIG. 3A, but plural lines 232$j$ of trees, with j being a natural number. Note that in this embodiment, the same optical fiber 220 extends along each line 232$j$ of trees 230$i$.

Figure 3B:
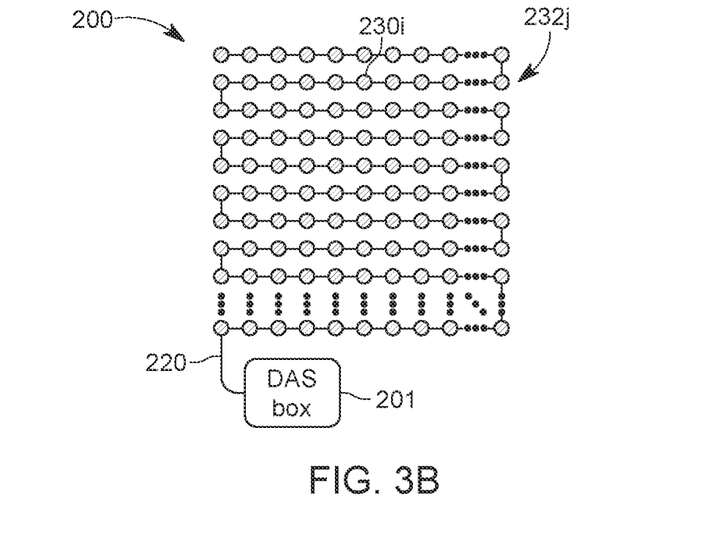
Figure 3C:
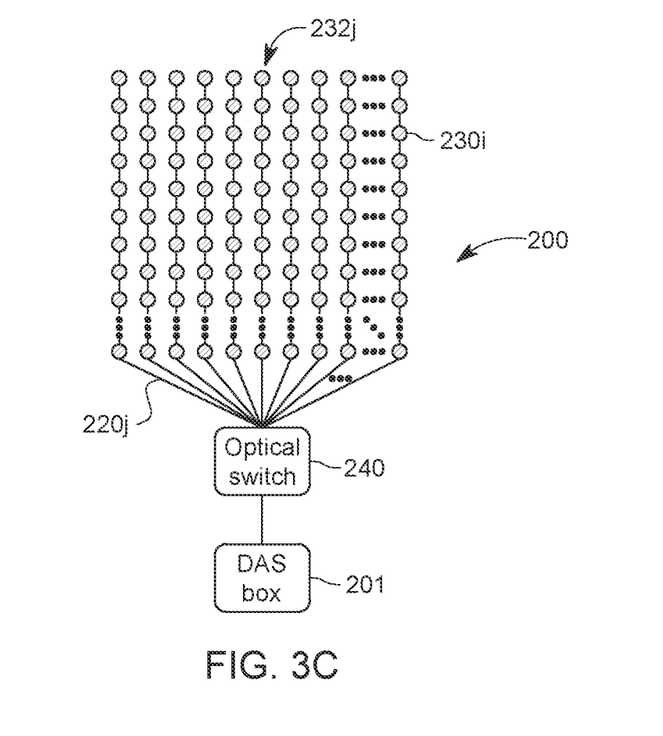

In yet another embodiment illustrated in FIG. 3C, plural optical fibers 220$j$ are distributed from a single DAS box 201, to plural lines 232$j$ of trees 230$i$. An optical switch 240 may be used to connect each optical fiber 220$j$ to a corresponding line 232$j$ of trees 230$i$. The optical switch 240 may be programmed to connect each optical fiber 220$j$, for a given time, to the DAS box 201, enough to get information to determine whether RPW are present in the trees or not. In this regard, note that there is no need to monitor the entire day a line of trees or a single tree for determining that RPW are present. Intermittent monitoring of the trees, for example, every hour or every couple of hours or even every day or every couple of days could be enough for determining the RPW presence. In one application, time multiplexing may be implemented over the optical switch 240 for optical switching.

Thus, the topology of the optical fiber DAS network, as illustrated in FIGS. 3A to 3C is quite flexible and can be adapted to fit almost any spatial distribution of palm trees in a small or large farm. If the sum of the separations between consecutive trees, including the lengths of the optical fibers wounded around trees, is within the sensing range of the DAS system 200, one optical fiber is sufficient to cover the whole farm, as illustrated in FIGS. 3A and 3B. Otherwise, for extremely large farms, multiple optical fibers 220$j$ can be connected through an optical switch to the DAS box, as illustrated in FIG. 3C. Because the sensing speed is not a considerable factor in this application, rotating the optical switch 240 around the different fibers 230$j$ would provide continuous monitoring to the whole farm.

Figure 3D:
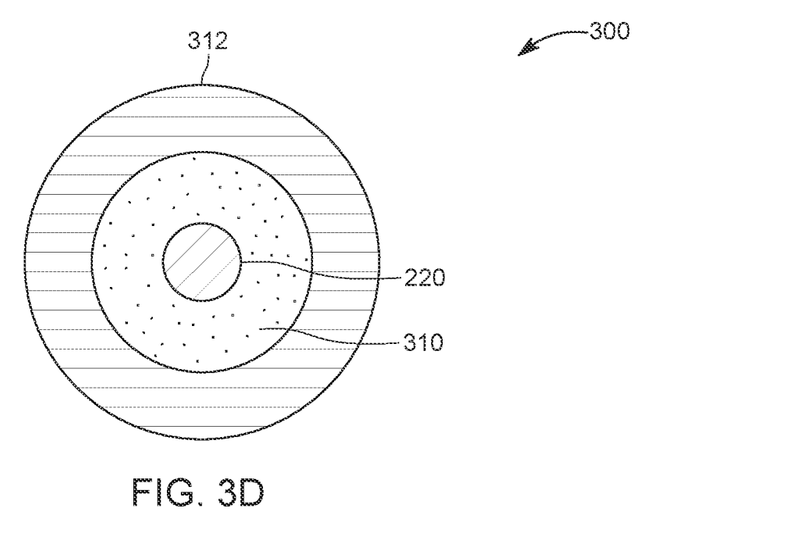
Figure 3E:
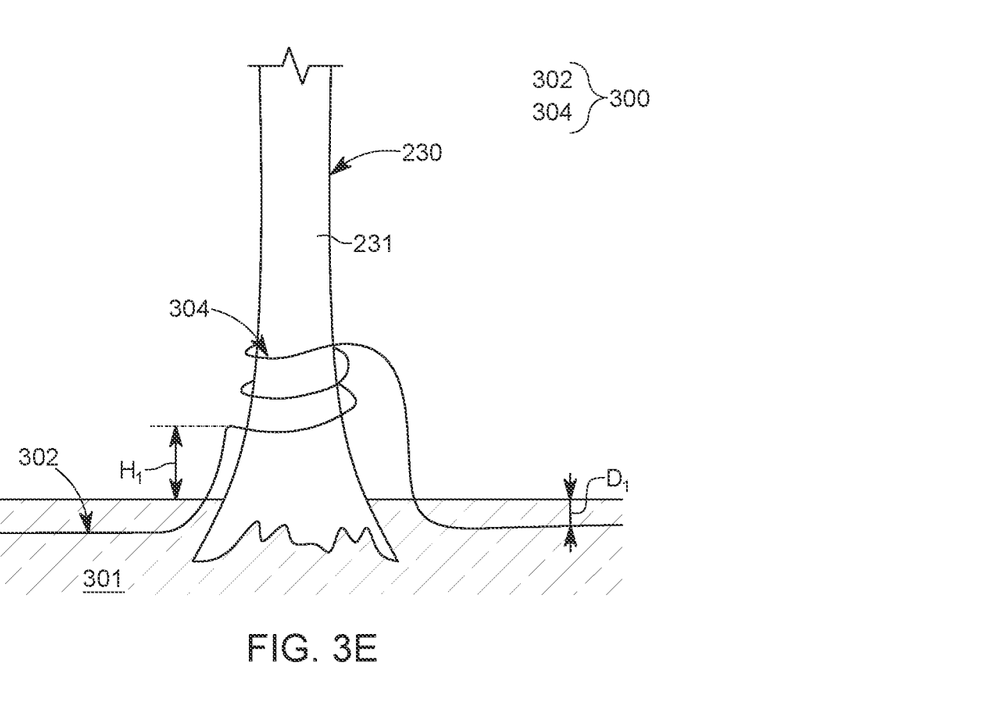

The optical fiber 220 may be wounded around the trunk of the tree 230 by itself, as shown in FIG. 3A, or protected by a cover layer as illustrated in FIGS. 3D and 3E. More specifically, FIG. 3D shows the optical fiber 220 being completely surrounded by a filler material 310, for example, cotton or similar fiber material, and an exterior shield layer 312. This optical fiber assembly 300 may have the exterior shield layer 312 made to fully enclose the filler material and the optical fiber. The exterior shield layer 312 may be made from a rigid material (e.g., steel tube or pipe, plastic pipe) or from a flexible material (e.g., flexible metallic or plastic pipe, etc.). In one embodiment, the exterior shield layer 312 is rigid fora portion of the optical fiber and flexible for another portion of the optical fiber.

For example, as illustrated in FIG. 3E, the optical fiber assembly 300 has a first portion 302 that is fully buried in the ground 301, and a second portion 304 that is wounded around the trunk 231 of the tree 230. The first portion 302 may be made to be rigid while the second part 304 may be made to be flexible, to allow it to wound around the trunk of the tree. The purpose of the filler material and the exterior shield layer 312 is to protect the optical fiber 220 from mechanical or thermal damage while being deployed in the field. In this regard, note that in a farm there is heavy equipment that move around the trees for various agricultural procedures. In one application, the depth D1 at which the first portion 302 is buried into the ground is between 0.5 to 2 m. A height H1 at which the optical fiber assembly starts to wound around the trunk 231 is about 0.5 to 3 m for best efficiency, as the weevil larva tends to attack the trunk at these heights. A length of the optical fiber 220 that is present in the second portion 304 is between 1 and 10 m. Other numbers for the parameters discussed herein may be used. However, one or more portions of the optical fiber may be directly exposed to the ambient, at desired locations between the trees, to be able to detect the temperature and moisture of the ambient.

Figure 4:
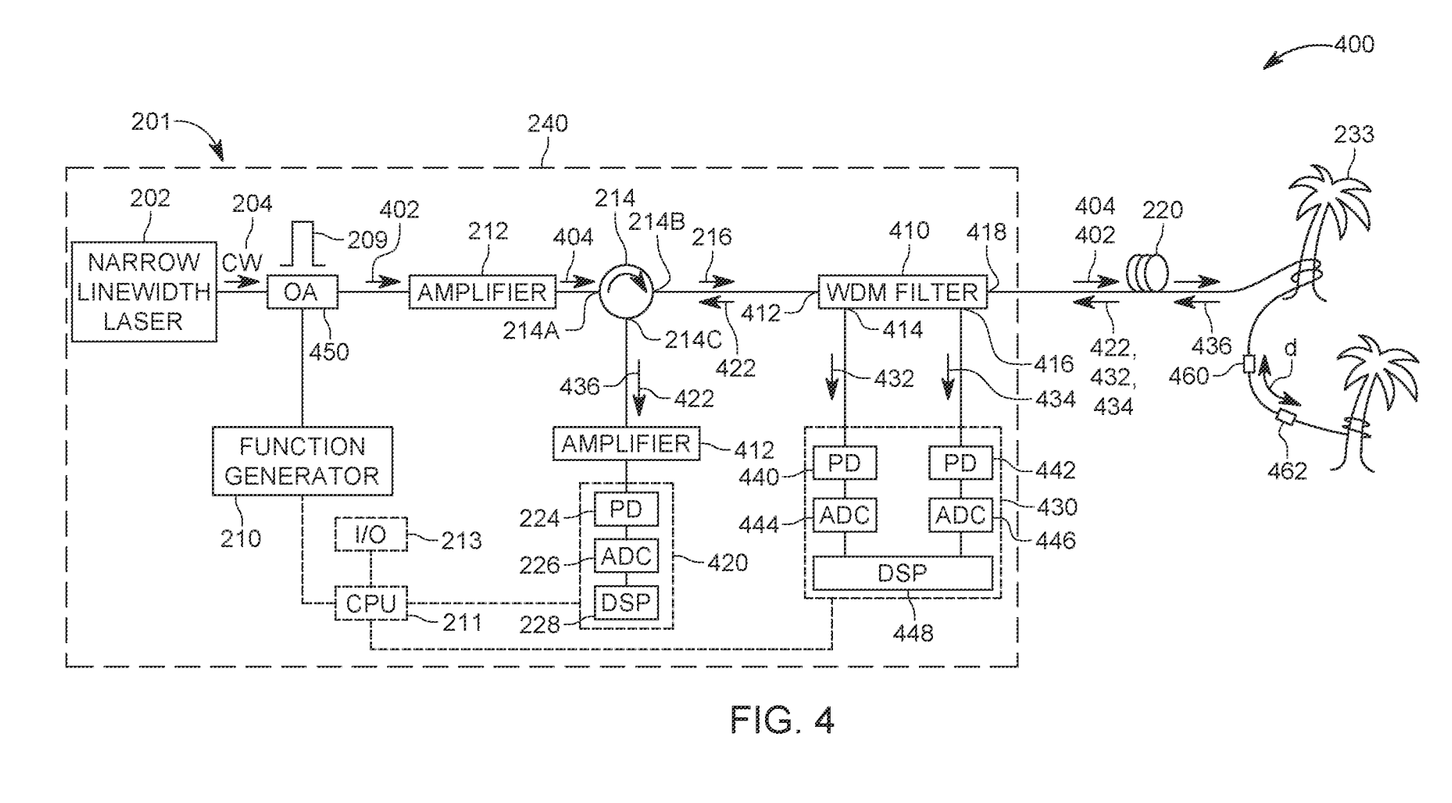
FIG. 4 shows a modified distributed acoustic sensor system that has not only a red palm weevil detection capability, but also temperature and moisture capabilities.

While the embodiment illustrated in FIG. 2 was configured to detect only the Rayleigh scattered light, the embodiment illustrated in FIG. 4 is configured to also detect the Stokes Raman backscattering, the Anti-Stokes Raman backscattering, and also the fiber Bragg gratings (FBGs) pulses, as now discussed in more detail. The system 400 also has a single housing 240 (the DAS box 201) that includes many of the elements shown in FIG. 2 (those elements are not repeated herein), but also new elements, such as a wavelength-division-multiplexing (WDM) filter 410, an amplifier 412 located between the circulator 214 and the RPW detection and moisture monitoring unit 420, and the fire detection unit 430. The modulator 208 in FIG. 2 is replaced with an optical amplifier (OA) 450, which may be implemented as a semiconductor optical amplifier (SOA) or a super-luminescent diode (SLD). An optical amplifier is a device that directly amplifies an optical signal without transforming it first into an electrical signal.

The narrow linewidth laser 202 produces a continuous wave (CW) light 204, which is then modulated into time-domain optical pulses 402 using the optical amplifier 450, which is driven by the function generator 210. The laser 202 is selected to generate a CW light 204 having a single wavelength, e.g., between 1520 and 1575 nm, with a preferred range of 1550 to 1560 nm. The modulated pulses 402 are optionally amplified by amplifier 212 and then injected via the circulator 214 into the WDM filter 410. In one embodiment, the WDM filter 410 includes three input ports, Rayleigh port 412, Stokes Raman port 414, and Anti-Stokes Raman 416, and one output common port 418.

Because the Rayleigh scattering is an elastic phenomenon, which means it occurs at the same wavelength as the pumped signal 402, the optical pulses are injected into the WDM filter 410 through the Rayleigh scattering input port 412. The output common port 418 of the WDM filter 410 is connected to the optical fiber 220 that extends to the trees 233, as illustrated in FIG. 4. While the optical pulses 402 are traveling forward through the optical fiber 220, the Rayleigh signal 422, the Stokes Raman signal 432, and the Anti-Stokes Raman signal 434 are backscattered, as also shown in FIG. 4. Because the three backscattered signals 422, 432, and 434 have different wavelengths (the Rayleigh signal has the same wavelength as the input pulse 402, as the Rayleigh signal is produced as a result of an elastic scattering, while the Stokes Raman and Anti-Stokes Raman signals have different wavelengths due to their inelastic scattering origin), they can be well separated via the WDM filter 410 such that the Rayleigh signal 422 is directed via the circulator 214 to the amplifier 412 and the RPW detection unit 420, for acoustic sensing, while the Stokes and Anti-Stokes Raman signals 432 and 434 are sent to the fire detection unit 430 for temperature sensing (fire detection). Using the amplifier 412 is optional and depends on the Rayleigh signal 422 power level.

The Rayleigh signal 422 is detected by the photodetector 224, processed with the analog-to-digital converter 226, and finally the digital signal processor 228 is used for early detection of RPW, as discussed, for example, in PCT International Application No. PCT/IB2020/053728, the entire content of which is incorporated herein by reference. On the other hand, the filtered Stokes and Anti-Stokes Raman signals 432 and 434 are routed through ports 414 and 416 of the WDM filter 410, respectively, to the fire detection unit 430, where each signal is received at corresponding PD 440 and 442, digitized at corresponding ADCs 444 and 446, and finally processed at a common DSP 448 for obtaining the temperature along the optical fiber. Thus, for monitoring the presence of the RPW and fires in the farm, the various return signals 422, 432, and 434 are distributed to the RPW detection and moisture monitoring unit 420 and also to the fire detection unit 430, which are both part of the DAS box 201, as shown in FIG. 4. The Rayleigh signal 422 and the Stokes Raman and Anti-Stokes Raman signals 432 and 434 are a consequence of sending a same CW light pulse 204 through the optical fiber 220.

However, to monitor the moisture along the optical fiber 220, the narrow linewidth laser 202 is switched off, so that the CW light pulse 204 is not generated. Under this scenario, the OA 450 generates optical pulses 404 having a broadband spectrum, e.g., between 1530 and 1565 nm. The optical pulses 404 are then optionally amplified in amplifier 212 and directed via the circulator 214 to the WDM filter 410's Rayleigh input port 412. Afterwards, the pulses 404 are delivered through the WDM filter's common output port 418 to the optical fiber 220. The optical fiber 220 has at least two fiber Bragg gratings (FBGs) 460 and 462 written in it. The two FBGs 460 and 462 act as a moisture sensor. The locations of the FBGs 460 and 462 along the optical fiber 220 are selected where the moisture is required to be monitored. A distance d between the two FBGs 460 and 462 along the optical fiber 220 is selected to be around 1 m, but not larger than 5 m. Because the FBGs 460 and 462 reflect light without shifting the wavelength, the reflected signals 436 from the FBGs 460 and 462 are collected via the WDM filter's Rayleigh input port 412. Similarly to the Rayleigh signals, the FBGs 460 and 462' reflected signals 436 are routed with the circulator 214 towards the PD 224 and ADC 226 for detection, and eventually the DSP 228 produces the moisture sensing parameters. It is noted that the FBGs signals 436 are processed in this embodiment in the RPW detection and moisture monitoring unit 420, where the Rayleigh signals 422 are processed.

While the DAS box 201 provides distributed acoustic and temperature sensing along the optical fiber, the FBG-based sensors offer quasi-distributed moisture sensing at the locations where the FBGs are built into the optical fiber. In other words, the acoustic and temperature sensing can take place anywhere along the optical fiber while the moisture detection can take place only at given locations, where the optical fiber was provided with the FBGs. Note that at least two FBGs need to be present into the optical fiber, one reference FBG and one moisture sensing FBG, for being able to monitor the moisture. The reference FBG may be encapsulated into a specific material so that its moisture content does not change irrespective of the ambient conditions. However, the other FBG, the moisture detection FBG, needs to be sensitive to the ambient, and thus, is capable of generating a signal that is affected by the ambient moisture.

Figure 5A:
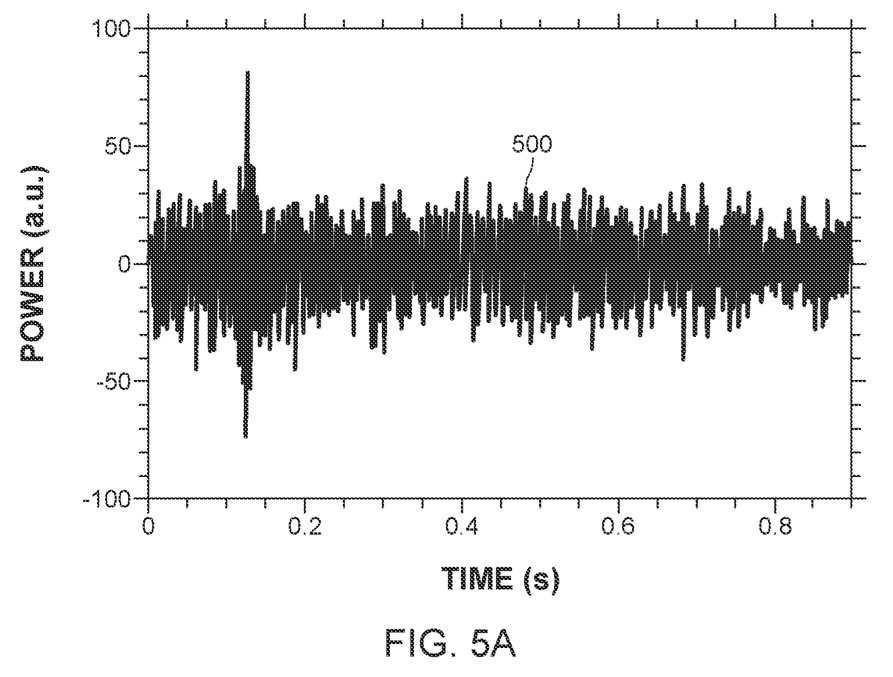
FIGS. 5A and 5B illustrate the sound signature of the larva when recorded with an optical fiber, in the time domain and the frequency domain, respectively.
Figure 5B:
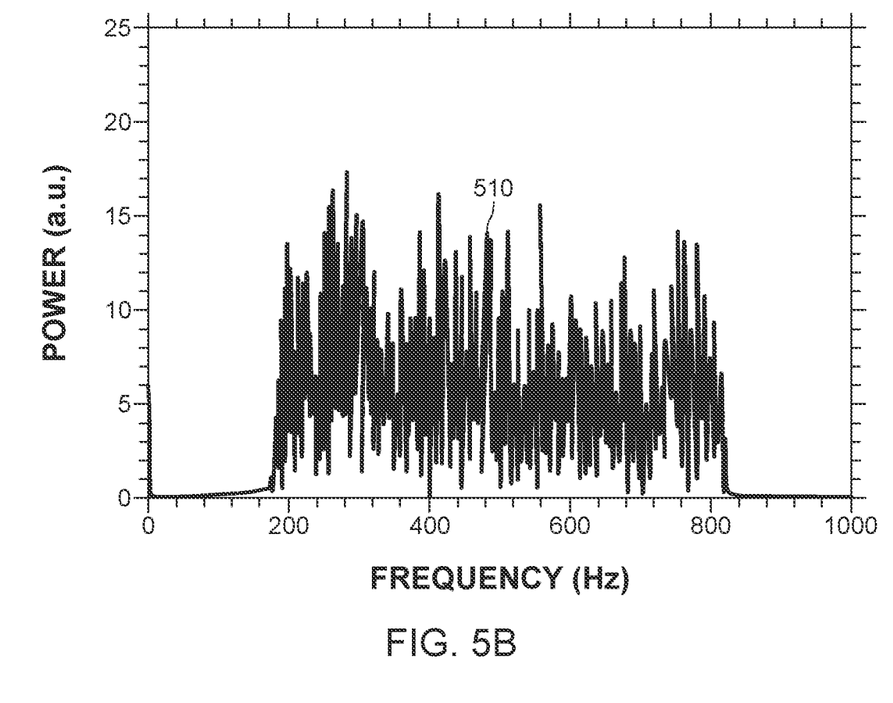

The versatile optical fiber sensor 220 is used to simultaneously detect RPW, fires, and moisture changes as now discussed. For the purpose of early detection of RPW, the DAS system 400 can "hear" the RPW's eating sound via processing of the Rayleigh signals, as disclosed [1] and [2]. In particular, the optical fiber DAS 220 is used for (1) locating the acoustic signal source associated with the RPW, and (2) calculating the frequency of the acoustic signal. The first feature (1) is achieved via subtracting the Rayleigh traces in the time domain, while the second feature (2) is determined by calculating the Fourier transform of the acoustic signal. The eating sound of the RPW has frequency components that extend to roughly 800 Hz. In contrast, the other environmental noises, such as tree swinging by wind, have low frequency components which are typically less than 100 Hz. By applying a high- or band-bass filter in the frequency domain, as discussed in [2], the RPW sound can be extracted from the noise sources and the sensing unit can distinguish between the healthy and infested trees. In this respect, FIGS. 5A and 5B show representative examples for the signal 500 in the time-domain (FIG. 5A shows the power versus time recorded signal) and for the signal 510 in the frequency-domain (FIG. 5B shows the power versus the frequency signal) of the weevil larvae sound recorded by the system 400. As shown in FIG. 5B, the power spectrum of the larvae sound is calculated after applying a band-pass filter with the range [200 Hz,800 Hz].

Figure 6A:
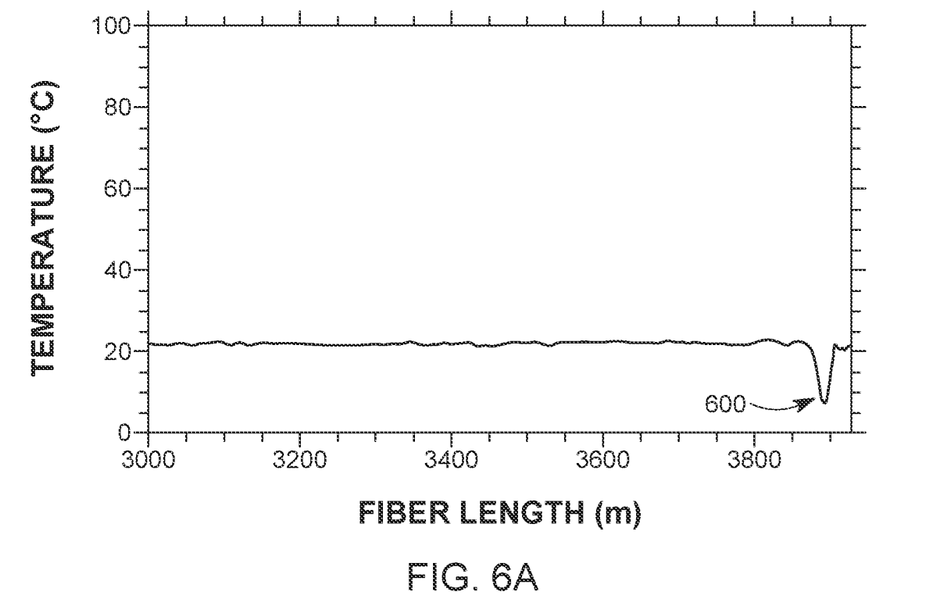
FIGS. 6A and 6B illustrate a low- and high-temperature detection point, respectively, with the same optical fiber.
Figure 6B:
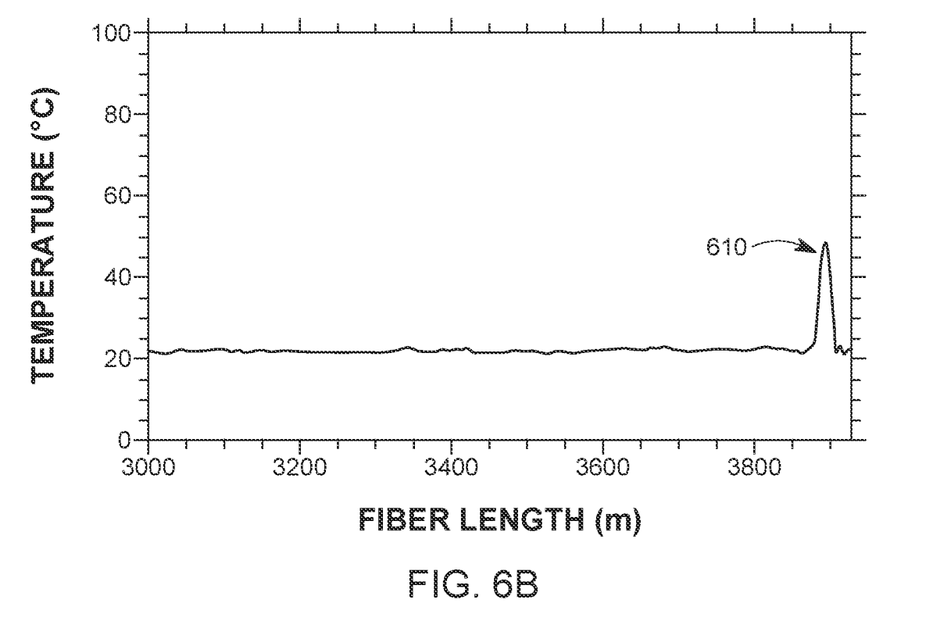

Regarding the fire detection functionality of the system 400, the Stokes and Anti-Stokes Raman signals are used for temperature sensing. The system 400 is initially calibrated by linking the ratio between the Anti-Stokes and Stokes Raman signals and the temperature to be measured, as discussed, for example, in [3]. In this respect, FIGS. 6A and 6B show two representative examples of temperature distributions recorded via the sensing unit 201, along the optical fiber 220. For these measurements, the entire fiber 220 was located at room temperature (~22° C.), and at a ~3,900 m distance from the start of the fiber, the ambient temperature was intentionally changed down, which resulted in the negative peak 600 shown in FIG. 6A, and then the temperature was changed up, which resulted in the positive peak 610, as shown in FIG. 6B. As illustrated in FIGS. 6A and 6B, the system 400 provides accurate measurements to the temperature values along the optical fiber 220 and, from these graphs, the location along the fiber where the temperature increases or decreases can be determined. Thus, as the farmer that uses the system 400 knows the exact location of the optical fiber(s) 220 in the farm, an increase in the temperature at any location of the optical fiber, over a given threshold, for example, 100° C., would signal the likely presence of a fire. Thus, the farmer would know exactly the location of the fire and can efficiently provide the necessary resources for suppressing the fire. In this regard, the processor 211, which is connected to each of the detection units inside the housing 240 in FIG. 4, can be configured to automatically determine when a sensed parameter is above or below a given threshold, and automatically send a message (e.g., text, email, phone call, etc.) to the farmer to alert her/him about the condition that occurred on the farm The system 400 can also perform quasi-distributed moisture measurements by using writing FBGs 460 and 462 along the optical fiber 220, where moisture is desired to be monitored. Wherever moisture is desired to be monitored, along the optical fiber 220, two FBGs (FBG 460 and FBG 460, as shown in FIG. 4) are made into the optical fiber. Note that FIG. 4 shows only two FBGs for simplicity, but any number of FBGs may be formed into the optical fiber. Also note that an FBG is a reflector used in waveguides, and it is formed from multiple layers of alternating materials with a varying refractive index, or by periodic variation of some characteristic (such as height) of a dielectric waveguide, resulting in a periodic variation in the effective refractive index in the guide. As a result of this structure, the incoming optical pulse 404 is reflected at the FBGs as optical pulse 436 and this reflected pulse is affected by the ambient moisture of the optical fiber. The FBGs are added to the optical fiber when the optical fiber is manufactured, and because it is inscribed into the internal structure of the optical fiber, the FBG is not visible by bare eye from the outside of the optical fiber.

Figure 7A:
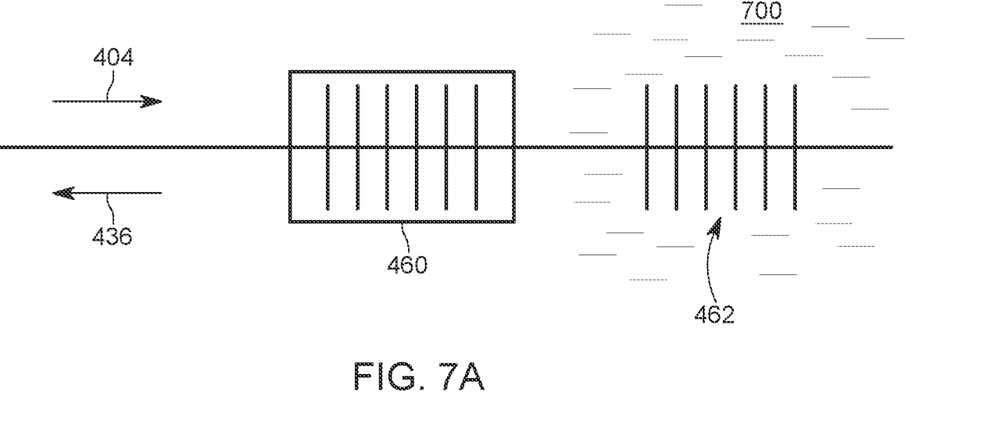
FIGS. 7A and 7B illustrate the placement of Fiber Bragg Gratings along the optical fiber for monitoring the moisture of the soil.
Figure 7B:
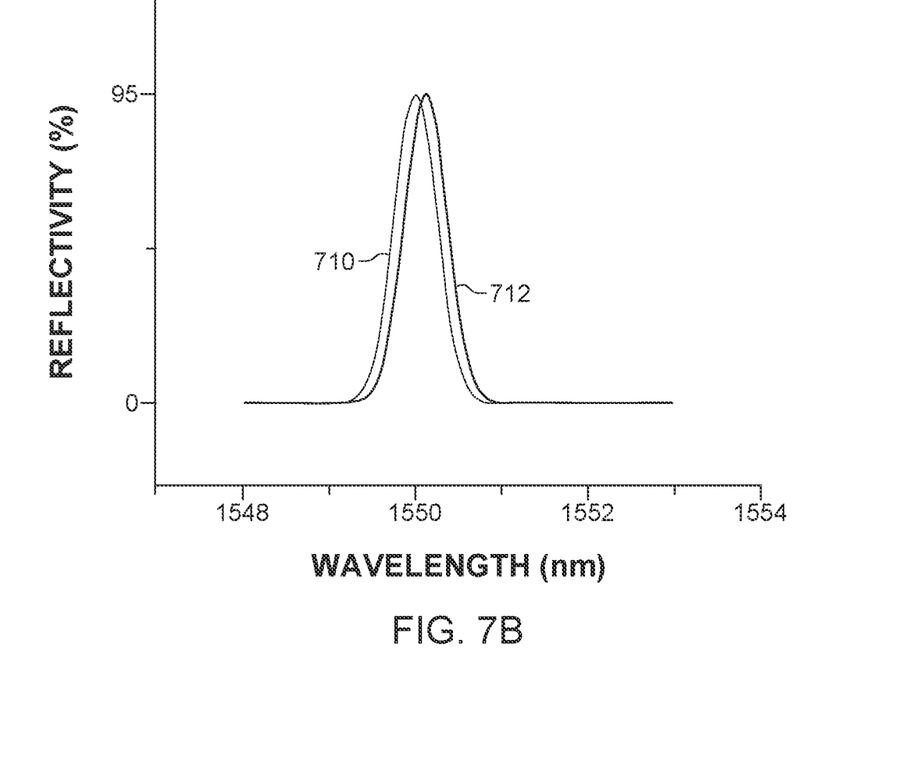

For determining the moisture at a desired location, the first FBG 460 is placed in a controlled environment (i.e., sealed inside the optical fiber so that no external moisture arrives at the first FBG), which means that the moisture level is well-controlled, i.e., does not change as the ambient level of moisture changes. This is illustrated in FIG. 7A, as the FBG 460 is schematically shown placed in a sealed box. The second FBG 462 can be implanted in the soil 700 for moisture measurement. Both of the FBG 460 and FBG 462 receive the input optical pulse 404 generated by the OA 450, and reflect back part of the input power as optical pulse 436, toward the DAS box 201, where either a photodetector or a spectrum analyzer is receiving them. As the soil moisture changes, the peak reflectivity 712 of the FBG 462 is shifted while the peak reflectivity 710 of the FBG 460 is kept fixed, as illustrated in FIG. 7B. The PD 224, or a spectrum analyzer, can detect the FBG 462's spectrum shift and the DSP 228 can evaluate the soil moisture value. Note that in order to map the spectrum shift to the actual moisture of the soil, the two FBGs 460 and 462 need to be first calibrated in a controlled environment.

Thus, the system shown in FIG. 4 is capable to determine not only the sound signature of the RPW by using the optical fiber 220 and the associated electronics, but also the presence of a fire, by measuring the temperature along the optical fiber, and also the moisture of the soil around the tree where the optical fiber is distributed. While the sound signature of the RPW and the temperature can be detected simultaneously, by using a same input narrow linewidth optical signal 402 generated by a laser device 202, the moisture is detected by using a broadband light signal 404, which is generated by the OA 450. The electronics used to measure all these parameters is integrated into the single DAS box 201, so that the system 400 includes only two externally visible components, the DAS box 201, and the optical fiber 220. This ensures that the user of the system can easily install and maintain the system.

Figure 8:
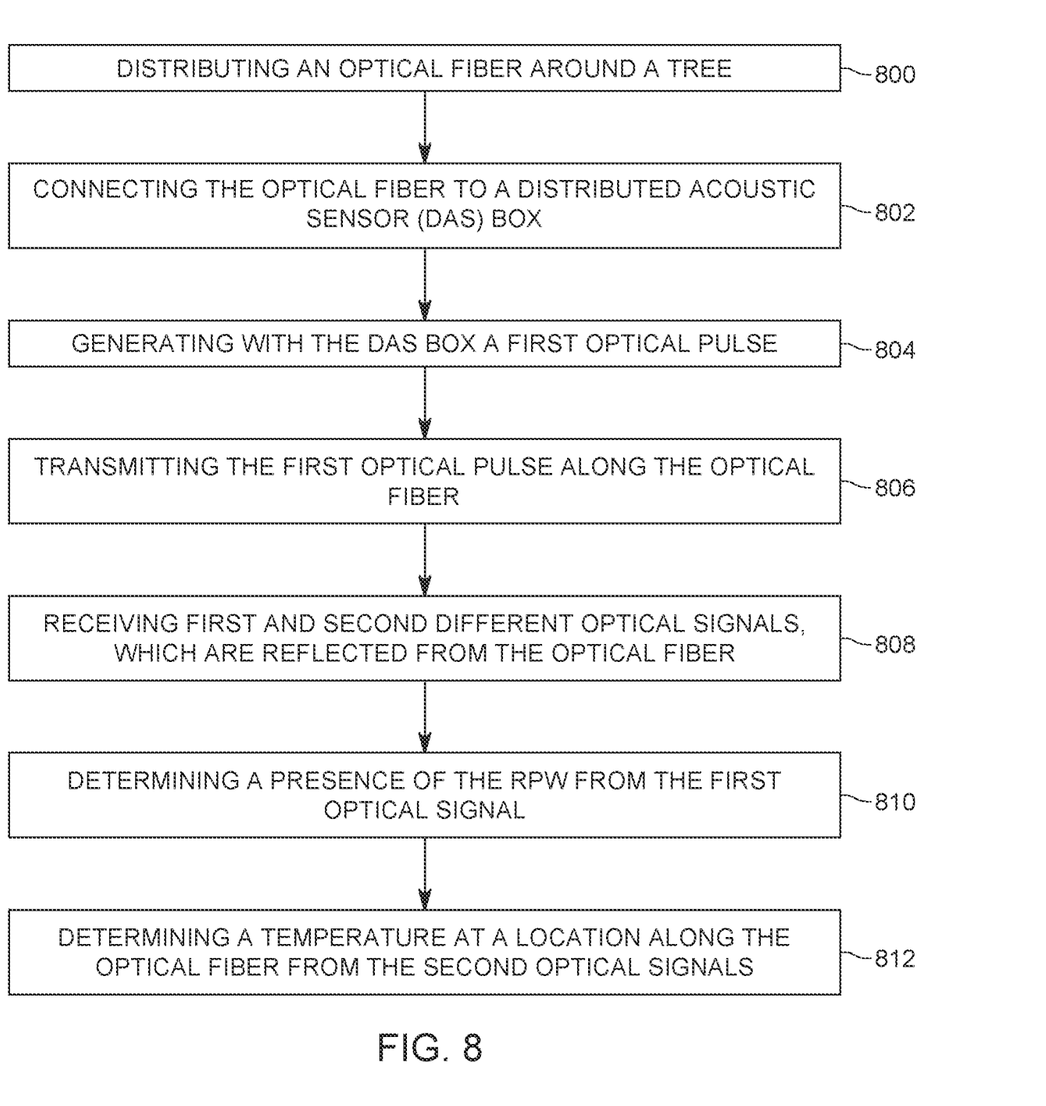
FIG. 8 is a flowchart of a method for determining when a tree is infected, and the temperature and moisture of the ambient of the tree, based on the DAS system.

A method for detecting red palm weevil, farm fire, and soil moisture is now discussed with regard to FIG. 8. The method includes a step 800 of distributing the optical fiber 220 around a tree, a step 802 of connecting the optical fiber 220 to the distributed acoustic sensor (DAS) box 201, a step 804 of generating with the DAS box 201 a first optical pulse 204, a step 806 of transmitting the first optical pulse 204 along the optical fiber 220, a step 808 of receiving first and second different optical signals 422, 430, 432, which are reflected from the optical fiber 220, a step 810 of determining a presence of the RPW from the first optical signal 422, and a step 812 of determining a temperature at a location along the optical fiber 220 from the second optical signals 430, 432. In one application, the method further includes switching off the first optical pulse, generating a second optical pulse, which is different from the first optical pulse, transmitting the second optical pulse along the optical fiber, to first and second Fiber Bragg Gratings (FBGs), receiving a third optical signal from the first and second FBGs, and determining a moisture at a location around the tree, from the third optical signal. In one application, the first optical signal is a Rayleigh signal 422, the second optical signal includes Stokes Raman and Anti-Stokes Raman signals 432, 434, and the third optical signal includes FBGs signals 436.

The disclosed embodiments provide an optical DAS system for monitoring tree infestation, and ambient temperature and moisture around the trees. It should be understood that this description is not intended to limit the invention. On the contrary, the embodiments are intended to cover alternatives, modifications and equivalents, which are included in the spirit and scope of the invention as defined by the appended claims. Further, in the detailed description of the embodiments, numerous specific details are set forth in order to provide a comprehensive understanding of the claimed invention. However, one skilled in the art would understand that various embodiments may be practiced without such specific details.

Although the features and elements of the present embodiments are described in the embodiments in particular combinations, each feature or element can be used alone without the other features and elements of the embodiments or in various combinations with or without other features and elements disclosed herein.

This written description uses examples of the subject matter disclosed to enable any person skilled in the art to practice the same, including making and using any devices or systems and performing any incorporated methods. The patentable scope of the subject matter is defined by the claims, and may include other examples that occur to those skilled in the art. Such other examples are intended to be within the scope of the claims.

REFERENCES

[1] I. Ashry, Y. Mao, M. S. Alias, T. K. Ng, F. Hveding, M. Arsalan, and B. S. Ooi, "Normalized differential method for improving the signal-to-noise ratio of a distributed acoustic sensor," Appl. Opt. 58, 4933 (2019).
[2] PCT International Application No. PCT/IB2020/053728.
[3] X. Ma, J. Chang, Z. Wang, W. Wang, and T. Li, "Using Multiple Reference Points in Raman Based Distributed Temperature Sensor for Eliminating DC Interference," 14, 295-301 (2014).

What is claimed is:

1. An integrated system for detecting a red palm weevil (RPW), farm fire, and soil moisture, the system comprising:
    an optical fiber configured to be extending to a tree; and
    a distributed acoustic sensor (DAS) box connected to the optical fiber, wherein the DAS box includes a first digital signal processor, a second digital signal processor, different from the first digital signal processor, and a wavelength-division-multiplexing (WDM) filter,
    the WDF filter is configured to filter a reflected optical signal, from the optical fiber, to generate first to third different optical signals,
    the first optical signal is routed to the first digital signal processor to determine a presence of the RPW,
    the second optical signals are routed to the second digital signal processor to determine a temperature at a location along the optical fiber, and
    the third optical signal is routed to the first digital signal processing to determine a moisture at a location around the tree.

2. The system of claim 1, wherein the first optical signal is a Rayleigh signal, which is reflected in the optical fiber, the second optical signals include Stokes Raman and Anti-Stokes Raman signals reflected in the optical fiber, and the third optical signal includes Fiber Bragg Gratings (FBGs) signals generated by FBGs formed in the optical fiber.

3. The system of claim 1, wherein the first and second optical signals are simultaneously propagating through the optical fiber while the third optical signal is off, and the third optical signal is propagating through the optical fiber when the first and second optical signals are off.

4. The system of claim 1, wherein the DAS box comprises:
    a laser device configured to generate a first optical pulse, which, after propagating through the optical fiber, generates the first and second optical signals, and
    an optical amplifier configured to generate a second optical pulse, which is different from the first optical pulse, and after the second optical pulse propagates through the optical fiber, generates the third optical signal.

5. The system of claim 4, wherein the optical amplifier is optically connected to the laser device and is configured to amplify the first optical pulse.

6. The system of claim 4, wherein the WDM filter has first to third input ports and a common output port,
    wherein the common output port is connected to the optical fiber and is configured to pass along the first to second optical pulses, and
    wherein the WDM filter provides the first optical signal to the first input port, the second optical signals to the second and third input ports, and the third optical signal to the first input port.

7. The system of claim 6, wherein the first input port is optically connected to an RPW detection and moisture monitoring unit, and the second and third input ports are optically connected to a fire detection unit.

8. The system of claim 7, wherein the RPW detection and moisture monitoring unit receives the first optical signal to determine the RPW presence and also receives the third optical signal to determine the moisture, while the fire detection unit receives the second optical signals to determine the temperature.

9. The system of claim 8, wherein each of the RPW detection and moisture monitoring unit and the fire detection unit includes a photodetector, an analog to digital converter, and one of the first and second digital signal processors.

10. The system of claim 1, wherein a first portion of the optical fiber is located underground, and a second portion of the optical fiber is located above ground.

11. An integrated system for detecting a red palm weevil (RPW), farm fire, and soil moisture, the system comprising:
an optical fiber including a pair of Fiber Bragg Gratings (FBGs), and configured to be extending to a tree; and
a distributed acoustic sensor (DAS) box connected to the optical fiber,
wherein the DAS box includes a first digital signal processor, a second digital signal processor, different from the first digital signal processor, and a wavelength-division-multiplexing (WDM) filter,
the WDM filter is configured to filter a reflected optical signal from the optical fiber to generate a Rayleigh signal, Stokes Raman and Anti-Stokes Raman signals, and FBGs signals generated by the pair of FBGs,
the DAS box includes a first digital signal processor configured to process the Rayleigh signal to determine a presence of the RPW,
the DAS box further includes a second digital signal processor, different from the first digital signal processor, and configured to process the Stokes Raman and Anti-Stokes Raman signals to determine a temperature at a location along the optical fiber, and
the first digital signal processor is also configured to process the FBGs signals to determine a moisture at a location around the tree.

12. The system of claim 11, wherein the DAS box comprises:
a laser device configured to generate a first optical pulse, which after being reflected in the optical fiber, generates the Rayleigh signal, and also generates the Stokes Raman and Anti-Stokes Raman signals, and
an optical amplifier configured to generate a second optical pulse, which after being reflected from the pair of Fiber Bragg Gratings (FBGs), generates the FBGs signals.

13. The system of claim 12, wherein the optical amplifier is optically connected to the laser device and is configured to amplify the first optical pulse.

14. The system of claim 13, wherein the WDM filter has first to third input ports and a common output port,
wherein the common output port is connected to the optical fiber and is configured to pass along the first and second optical pulses, and
wherein the WDM filter provides the first optical signal to the first input port, the second optical signals to the second and third input ports, and the third optical signal to the first input port.

15. The system of claim 14, wherein the first input port is optically connected to an RPW detection and moisture monitoring unit, and the second and third input ports are optically connected to a fire detection unit.

16. The system of claim 15, wherein the RPW detection and moisture monitoring unit receives the first optical signal to determine the RPW presence and also the third optical signal to determine the moisture, while the fire detection unit receives the second optical signals to determine the temperature.

17. The system of claim 16, wherein each of the RPW detection and moisture monitoring unit and the fire detection unit includes a photodetector, an analog to digital converter, and one of the first and second digital signal processors.

* * * * *